United States Patent [19]
Stanley et al.

[11] Patent Number: 5,855,908
[45] Date of Patent: Jan. 5, 1999

[54] NON-DISSOLVABLE DRUG-CONTAINING DOSAGE-FORMS FOR USE IN THE TRANSMUCOSAL DELIVERY OF A DRUG TO A PATIENT

[75] Inventors: Theodore H. Stanley, Salt Lake City; Brian Hague, West Valley City, both of Utah

[73] Assignee: University of Utah Research Foundation, Lake City, Utah

[21] Appl. No.: 339,655

[22] Filed: Nov. 15, 1994

Related U.S. Application Data

[60] Continuation of Ser. No. 152,414, Nov. 12, 1993, abandoned, which is a division of Ser. No. 403,752, Sep. 5, 1989, Pat. No. 5,288,498, which is a continuation-in-part of Ser. No. 60,045, Jun. 8, 1987, Pat. No. 4,863,737, which is a continuation-in-part of Ser. No. 729,301, May 1, 1984, Pat. No. 4,671,953.

[51] Int. Cl.$^6$ ..................................................... A61K 9/68
[52] U.S. Cl. .......................... 424/440; 424/439; 424/441; 514/948
[58] Field of Search .................................... 424/440, 441, 424/439; 514/948

[56] References Cited

U.S. PATENT DOCUMENTS

| | | | |
|---|---|---|---|
| 122,507 | 1/1872 | Wills | 514/948 |
| 1,430,642 | 10/1922 | Gross | 128/138 |
| 1,593,858 | 7/1926 | Venable | 90/16 |
| 1,847,415 | 3/1932 | Snell | 99/138 |

(List continued on next page.)

FOREIGN PATENT DOCUMENTS

| | | |
|---|---|---|
| 0001907 | 5/1979 | European Pat. Off. . |
| 1083896 | 9/1967 | United Kingdom . |
| 1171691 | 11/1969 | United Kingdom . |
| 4108841 | 5/1983 | United Kingdom . |

OTHER PUBLICATIONS

Brown, Absorption of Analgesics From the Buccal Mucous Membrane, 196 The Practitioner 125 (1966).

Beckett et al., "Buccal Absorption of Basic Drugs and Its Application as an In Vivo Model of Passive Drug Transfer Through Lipid Membranes", 19 J. Pharm. Pharmac, 31S (1967).

Dearborn et al., "Buccal Absorption as a Parameter of Analgesic Activity of Some P–substituted Acetanilides," 23 Journal Pharm.Pharmac. 73S (1971).

Dollery et al. "Differences in The Metabolism of Drugs Depending Upon Their Routes of Administration," 179 Annals of the New York Academy of Sciences 108 (1971).

Dopkin, "Buprenorphine Hydrochloride: Determination of Analgesic Potency," 24 Canadian Anaesthesiology Society Journal 186 (1977).

(List continued on next page.)

*Primary Examiner*—Raj Bawa
*Attorney, Agent, or Firm*—Workman, Nydegger & Seeley

[57] ABSTRACT

Compositions and methods of manufacture for producing a medicament composition capable of absorption through the mucosal tissues of the mouth, pharynx, and esophagus. The present invention relates to such compositions and methods which are useful in administering lipophilic and nonlipophilic drugs in a dose-to-effect manner such that sufficient drug is administered to produce precisely a desired effect. The invention also relates to manufacturing techniques that enable therapeutic agents to be incorporated into nondissolvable drug containment matrixes which are capable of releasing the drug within a patient's mouth. An appliance or holder is preferably attached to the drug containment matrix. Employing the present invention the drug may be introduced into the patient's bloodstream almost as fast as through injection, and much faster than using the oral administration route, while avoiding the negative aspects of both of these methods. The nondissolvable drug containment matrix may include permeation enhancers to increase the drug absorption by the mucosal tissues of the mouth. The matrix composition may also include pH buffering agents to modify the salival pH thereby increasing the absorption of the drug through the mucosal tissues.

5 Claims, 6 Drawing Sheets

U.S. PATENT DOCUMENTS

| | | | |
|---|---|---|---|
| 1,915,614 | 6/1933 | Parker | 99/138 |
| 1,971,560 | 8/1934 | Guyon | 90/16 |
| 2,096,611 | 10/1937 | Ellestad | 99/138 |
| 2,246,778 | 6/1941 | Cahoon | 99/138 |
| 2,295,042 | 9/1942 | Llewellyn | 43/34 |
| 2,323,656 | 7/1943 | Helfestein | 43/36 |
| 2,388,533 | 11/1945 | Edmondson et al. | 128/202 |
| 2,469,589 | 5/1949 | Barricini | 99/138 |
| 2,488,272 | 11/1949 | Davis | 57/154 |
| 2,499,734 | 3/1950 | Edmondson et al. | 128/197 |
| 2,508,560 | 5/1950 | Adams | 43/36 |
| 2,553,446 | 5/1951 | Edmondson et al. | 128/188 |
| 2,897,624 | 8/1959 | Yakel et al. | 43/36 |
| 2,915,061 | 12/1959 | Edmondson et al. | 128/188 |
| 2,926,121 | 2/1960 | Hobbs et al. | 424/440 |
| 2,963,404 | 12/1960 | Hammer et al. | 167/82 |
| 3,169,907 | 2/1965 | Heusser et al. | 424/440 X |
| 3,172,179 | 3/1965 | Schafer | 24/91 |
| 3,192,924 | 7/1965 | Edmondson et al. | 128/188 |
| 3,210,247 | 10/1965 | Suranyl | 514/270 |
| 3,264,115 | 8/1966 | Davis | 99/138 |
| 3,271,256 | 9/1966 | Frey | 167/82 |
| 3,344,030 | 9/1967 | Stevens et al. | 514/270 X |
| 3,399,673 | 9/1968 | Jones et al. | 128/188 |
| 3,418,743 | 12/1968 | Halvorsen | 43/35 |
| 3,429,308 | 2/1969 | Russell | 424/440 X |
| 3,493,652 | 2/1970 | Hartman | 424/435 X |
| 3,556,811 | 1/1971 | Smith | 99/134 |
| 3,797,494 | 3/1974 | Zaffaroni | 128/268 |
| 3,816,953 | 6/1974 | Hameen-Anttila | 43/35 |
| 3,867,927 | 2/1975 | Hergott | 128/15 |
| 3,943,928 | 3/1976 | Lariccia et al. | 128/260 |
| 3,996,934 | 12/1976 | Zaffaroni | 128/268 |
| 4,060,084 | 11/1977 | Chandrasekaran et al. | 128/260 |
| 4,093,709 | 6/1978 | Choi et al. | 424/19 |
| 4,131,648 | 12/1978 | Choi et al. | 424/22 |
| 4,138,344 | 2/1979 | Choi et al. | 252/1 |
| 4,139,627 | 2/1979 | Lane et al. | 424/267 |
| 4,168,308 | 9/1979 | Wretlind et al. | 514/270 X |
| 4,169,885 | 10/1979 | Raaf et al. | 424/435 |
| 4,226,848 | 10/1980 | Nagai et al. | 424/440 X |
| 4,292,299 | 9/1981 | Suzuki et al. | 424/440 X |
| 4,307,075 | 12/1981 | Martin | 424/28 |
| 4,311,722 | 1/1982 | Vink et al. | 424/440 |
| 4,346,709 | 8/1982 | Schmitt | 128/260 |
| 4,372,942 | 2/1983 | Cimiluca | 424/16 |
| 4,389,393 | 6/1983 | Schor et al. | 424/441 |
| 4,390,520 | 6/1983 | Nagai et al. | 424/28 |
| 4,452,825 | 6/1984 | Klacik et al. | 424/440 |
| 4,466,953 | 8/1984 | Keith et al. | 424/28 |
| 4,470,962 | 9/1984 | Keith et al. | 424/28 |
| 4,482,534 | 11/1984 | Blank | 424/28 |
| 4,485,087 | 11/1984 | Otsuka et al. | 424/28 |
| 4,515,769 | 5/1985 | Merritt et al. | 424/440 |
| 4,517,173 | 5/1985 | Kizawa et al. | 424/435 |
| 4,529,589 | 7/1985 | Davydov et al. | 424/440 X |
| 4,551,329 | 11/1985 | Harris et al. | 424/22 |
| 4,572,832 | 2/1986 | Kigasawa et al. | 424/440 X |
| 4,588,580 | 5/1986 | Gale et al. | 424/21 |
| 4,671,953 | 6/1987 | Stanley et al. | 424/440 |
| 4,749,575 | 6/1988 | Rotman | 424/440 |
| 4,885,173 | 12/1989 | Stanley et al. | 424/440 |

OTHER PUBLICATIONS

Edge et al., "Analgesic Effects of Sublingual Buprenorphine," 34 Anaesthesia 463 (1979).

Fry, "Relief of Pain After Surgery," 34 Anaesthesia 549 (1979).

Bullingham et al, "Sublingual Buprenorphine Used Postoperatively: Clinical Observations and Preliminary Pharmacokinetic Analysis," 12 Br. J. Clin. Pharmac. 117 (1981).

Ellis et al., "Pain Relief After Abdominal Surgery—A Comparison of I.M. Morphine, Sublingual Buprenorphine and Self–Administer I.V. Pethidine," 54 Br. J. Anaesth. 421 (1982).

Port et al., "Topical Narcotic Anesthesia," 59 Anesthesiology (1983).

Windholz et al., "The Merck Index," published by Merck & Co., Inc., pp. 575, 795, 796, and Appendix 3 (1983).

Abrams, "New nitrate delivery systems" Buccal nitroglycerin, vol. 105 American Heart Journal, pp. 848–854 (1983).

White et al. "Comparative Pharamocology of Intravenous Anesthetics —A Model for Determining Dosage Requirements and Therapeutic Concentration Ranges During Surgery," 59 Anesthesiology, A379 (1983).

Asthana et al., "Verapamil Disposition and Effect on PQ–Intervals After Buccal, Oral and Intravenous Administration," Arzneim.–Forsch./Drug Res., pp. 498–502 (1984).

Derbyshire et al., "Non–Parenteral Postoperative Analgesia," Anesthesia 39, pp. 324–328 (1984).

DeBoer et al., "Drug Absorption by Sublingual and Rectal Routes," 56 British Journal of Anaesthesiology 69 (1984).

Stanley et al., "The Effect of Population Habits on Side Effects and Narcotic Requirements During High–Dose Fentanyl Anaesthesia," 31 Can Anaesth Soc J 398 (1984).

Bailey et al., "Anesthetic Induction with Fentanyl, " 64 anesth Analg 48 (1985).

Huttel et al., "Sublingual unitrazepam for Premedication," Acta Anaesthesiol Scnd. 29, pp. 209–211 (1985).

Risbo et al., "Sublingual Buprenorphine for Premedication and Postoperative Pain Relief in Orthopedic Surgery," Acta Anaesthesiol Scand. 29, pp. 180–182 (1985).

Risbo et al., "Sublingual Buprenorphine for Premedication and Postperative Pain Relief in Orthopedic Surgery," Acta Anaesthesiol Scand. 29, pp. 180–182 (1985).

Bell et al., "Buccal Morphine—A New Route for Analgesia?" The Lancet 71 (1985).

Schechter et al., "Status of Pediatric Pain Control: A Comparison of Hospital Analgesic Usage in Children and Adults," 77 Pediatrics 11 (186).

Bailey et al., "Pharmacology of Intravenous Narcotic Anesthetics,"in Anesthesia 2nd ed. (Miller ed. 1986).

Forbes et al., "2% Rectal Methohexital for Induction of Anesthesia in Children," vol. 65 Anesthesiology No. 3 (Sep. 1986).

Newspaper article entitled "Insulin Shots May Soon be Replaced by a Nasal Spray," Friday, Sep. 26, 1986 (UPI).

"New Drugs/Drug News," Hospital Therapy, pp. 9, 10,and 15 (Nov. 1986).

Davis, "Parenteral Therapy Techniques–Abstracts," Hospital Pharmacy, vol. 21, pp. 1171–1178 (Dec. 1986).

"Personalized Dosing and Effective Drugs can Control Emesis,"Pharmacy Practice News, p. 11 ( Mar. 1987).

"Administration of Drugs by the Buccal Route," The Lancet, pp. 666–667 (Mar. 21, 1987).

Lee, "Ophthalmic Delivery of Peptides and Proteins," Pharmaceutical Technology, pp. 26–38 (Apr. 1987).

Grover et al., "Low–does Intranasal Nitroglycerine Attenuates Pressor Reponse," 66 Anesthesiology, p. 722 (1987).

White et al., "Comparative Pharamacology of Intravenous Anesthetics —A Model for Determining Dosage Requirements and Therapeutic Concentration Ranges During Surgery," 59 Anesthesiology, A379 (Sep. 1983).

Stanley et al., "The Effect of Population Habits on Side Effects and Narcotic Requirements During High–Dose Fentanyl Anaesthesia," 31 Can Anaesth Soc J, 398 (1984).

Bailey et al., "Anesthetic Inductionwith Fentanyl," 64 Anesth Analg, 48 (1985).

Stanley et al., "Management of Pain and Pain–Related Problems in the Critically Ill Patent," Critical Care, State of the Art, vol. 6 (1985).

Schechter et al., "Status of Pediatric Pain Control: A Comparison of Hospital Analgesic Usage in Children and Adults" 77 Pediatrics 11 (1986).

Bailey and Stanley, "Pharmacology of Intravenous Narcotic Anesthetics in Anesthesia," 2nd ed. (Miller ed. 1986).

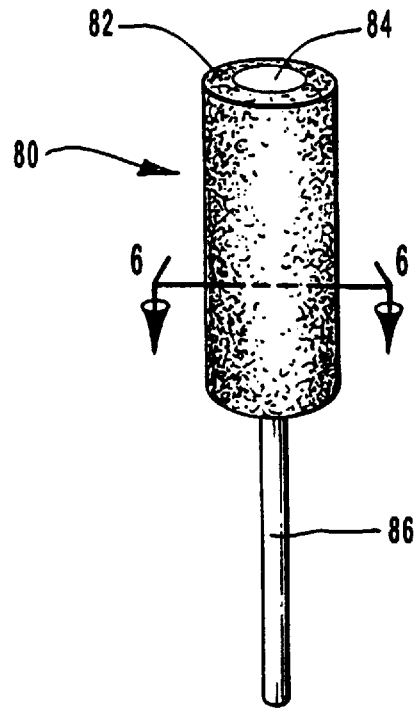
FIG. 5
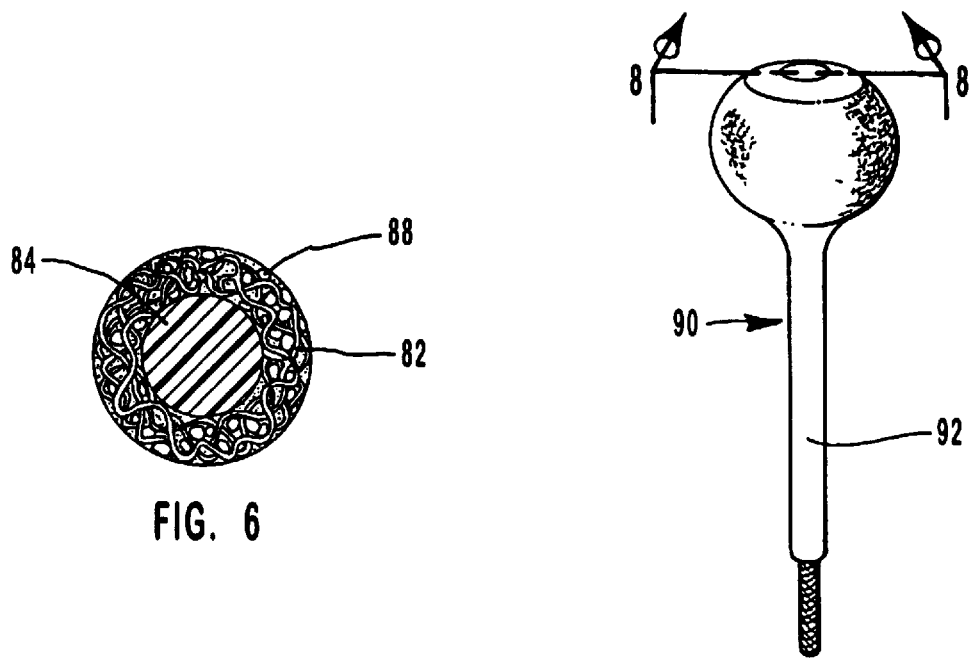
FIG. 6
FIG. 7

NON-DISSOLVABLE DRUG-CONTAINING DOSAGE-FORMS FOR USE IN THE TRANSMUCOSAL DELIVERY OF A DRUG TO A PATIENT

This application is a continuation of U.S. application Ser. No. 08/152,414, filed Nov. 12, 1993, for COMPOSITIONS AND METHODS OF MANUFACTURE OF ORAL NON-DISSOLVABLE MATRIXES FOR TRANSMUCOSAL ADMINISTRATION OF MEDICAMENTS, now abandoned, which is a divisional of application Ser. No. 07/403,752, filed Sep. 5, 1989, now U.S. Pat. No. 5,288,498 which is a continuation-in-part of application Ser. No. 07/060,045 filed Jun. 8, 1987 now issued as U.S. Pat. No. 4,863,737, which is a continuation-in-part of application Ser. No. 06/729,301 filed May 1, 1985, now issued as U.S. Pat. No. 4,671,953.

BACKGROUND

1. The Field of the Invention

The present invention relates to compositions and methods of manufacture of oral nondissolvable matrixes for medicaments used in the buccal, sublingual, pharyngeal, and esophageal transmucosal delivery of the medicaments. More particularly, the present invention is directed to compositions, and methods and apparatus for producing such compositions, for non-invasive administration of dose-to-effect amounts of medicaments through the mucosal tissues of the mouth, pharynx, and esophagus.

2. Related Applications

This application is a continuation-in-part application of copending application Ser. No. 07/060,045, filed Jun. 8, 1987, in the names of Theodore H. Stanley, M.D. and Brian Hague, and entitled "COMPOSITIONS AND METHODS OF MANUFACTURE OF COMPRESSED POWDER MEDICAMENTS," now U.S. Pat. No. 4,863,737 which issued Sep. 5, 1989, which is a continuation-in-part of application Ser. No. 06/729,301, filed May 1, 1985, in the names of the inventors hereof, and entitled "METHODS AND COMPOSITIONS FOR NONINVASIVE ADMINISTRATION OF SEDATIVES, ANALGESICS, AND ANESTHETICS," now U.S. Pat. No. 4,671,953 which issued Jun. 9, 1987. That application and patent are incorporated herein by specific reference.

3. The Background of the Invention

Recently, numerous advancements have taken place in the field of pharmacology and pharmaceutics with respect to the administration of drugs to treat various conditions. Despite the tremendous advancements in the field, however, drugs continue to be administered using substantially the same techniques that have been used for many decades. The vast majority of pharmaceutical agents continue to be administered either orally or by injection. Nevertheless, it is frequently found in the art that neither of these administration routes are effective in all cases, and both administration routes suffer from several disadvantages.

Oral administration is probably the most prevalent method of administering pharmacological medicaments. The medicament is generally incorporated into a tablet, capsule, or a liquid base, and then swallowed. The oral administration modality is often preferred because of its convenience. In addition, oral administration is generally nonthreatening, painless, and simple to accomplish for most patients.

Nevertheless, oral administration of drugs suffers from several disadvantages. One disadvantage is that pediatric and geriatric patients frequently have difficulty swallowing pills and other solid dosage forms, and such patients often refuse to cooperate in swallowing a liquid medication in addition, for many medicaments, the act or swallowing the medicament often requires fluids and increases gastric volume and the likelihood of nausea and vomiting.

A further problem with oral administration is that the rate of absorption of the drug into the bloodstream after swallowing varies from patient to patient. The absorption of the drug is dependent upon the movement of the drug from the stomach to the small and large intestines and the effects of to secretions from these organs and on the resulting pH within the stomach and intestines. Anxiety and stress can dramatically reduce these movements and secretions, prevent or reduce the final effects of the drug, and delay onset of the drug's effects.

Most significant is the fact that there is normally a substantial delay between the time of oral administration and the time that the therapeutic effect of the drug begins. As mentioned above, the drug must pass through the gastrointestinal system in order to enter the bloodstream; this typically takes forty-five minutes or longer. As mentioned above, anxiety and stress often increase this delay.

For many applications, such as premedication before surgery or where immediate relief from pain or a serious medical condition or immediate effectiveness of the drug is required, this delay is unacceptable. In modern outpatient units and operating rooms where rapid turnover of patients is essential for cost containment, extensive delays in the action of a drug are simply unacceptable.

An additional disadvantage of oral administration is that many drugs almost immediately experience metabolism or inactivation. The veins from the stomach and the small and large intestines pass directly through the liver. Thus, drugs entering the bloodstream must first pass through the liver before distribution into the general blood circulation. More than sixty percent of most drugs (and essentially one hundred to percent of certain drugs) are removed from the patient's bloodstream during this "first pass" through the liver. The result is that oral administration is impractical for many drugs, particularly many central nervous system and many cardiovascular-acting drugs that are used for rapid onset in critical care situations, as a premedication prior to surgery, or for the induction of anesthesia.

Further, additional stress is placed on the liver as it removes the excess drug from the bloodstream. This is particularly severe if the drug treatment has been occurring over an extended period of time. The liver may become overloaded with the drug's metabolite which then must be excreted. As a result, there is an increased risk of hepatic or renal disorders.

Another difficulty encountered in administering drugs orally is that dosages are prepared or determined for use with an "average" patient. Most drugs have widely varying effects on different patients. These effects depend upon patient habits, subtle genetic differences between patients, blood volumes, age, and numerous other known and unknown factors. Introducing a bolus of drug orally does not provide the ability to control the precise dose needed to obtain the desired effect, rather the dose is estimated in order to produce an average effect in an average patient. The result may be underdosing or overdosing a particular patient.

Underdosing a patient because of a low susceptibility to the drug fails to evoke the response sought by the physician. Overdosing the patient can result in dangerous depression of vital body functions, especially the heart and lungs. This can cause prolonged respiratory depression (necessitating mechanical ventilation after surgery), cardiac depression, and cardiac arrest.

In order to avoid some of the disadvantages of oral administration, injection is frequently used. Injecting a drug (generally intravenously or intramuscularly), results in rapid entry of the drug into the patient's bloodstream. In addition, this type of delivery avoids the removal of large quantities of the drug by the patient's liver. As a result, less total drug is usually needed, compared to orally administered drugs. The drug instead becomes rapidly distributed to various portions of the patient's body before exposure to the liver.

Most patients, particularly children and geriatric adults, have an aversion to injections. In some patients, this aversion may be so pronounced as to make the use of injections a serious concern. Since intense psychological stress can exacerbate a patient's debilitated condition, it sometimes becomes undesirable to use injections where the patient is seriously ill or suffers from a debilitating condition or injury.

In addition, individual variations in susceptibility in the metabolism of various drugs (particularly drugs with central nervous system activity) are even more profound when utilizing the injection route. In many instances, to prevent overdosing, it is the practice to inject a patient with a lower than average dose and then supplement the dose with additional injections as necessary. This "titration" makes necessary the use of repeated injections, which in turn greatly increases stress on the patient. Again, a precise dose cannot be administered to produce a precise effect because the patient's response varies widely depending on the specific characteristics of the specific patient.

One common approach to preparing a patient for surgery is to orally administer a sedative or anxiolytic. Although quick onset of sedation or anxiolysis has not always been a critical factor, it is more so now. Changing practices, including the increased use of outpatient units for day surgery and the pressures for cost containment in modern medicine, dictate rapid onset of action and the use of an absolutely ideal dose in order to avoid increased costs of caring for patients with delayed recovery secondary to slightly overdosing with anesthesia. Effective oral administration of premedication drugs with central nervous system activity (which cause a rapid onset of sedation and anxiolysis without producing excessive sedation) is often difficult to accomplish.

Some investigators have suggested that it may be possible to administer medication through the buccal mucosa of the cheek pouch or by sublingual administration. See, U.S. Pat. No. 4,671,953 entitled "METHODS AND COMPOSITIONS FOR NONINVASIVE ADMINISTRATION OF SEDATIVES, ANALGESICS, AND ANESTHETICS." Such administration through the mucosal tissues of the mouth, pharynx, and esophagus of therapeutic drugs possesses a distinct usefulness. Administration of drugs by this route does not expose the drug to the gastric and intestinal digestive juices. In addition, the drugs largely bypass the liver on the first pass through the body, thereby avoiding additional metabolism and/or inactivation of the drug.

Generally the drugs which are administered by any of the methods described above have an unpleasant taste. As a result, in order to allow for buccal or sublingual administration through the oral mucosal tissues, it is also necessary to incorporate the drug into some type of pleasant tasting mass, such as a "candy" matrix.

In the manufacture of medicated candy products by existing methods, the therapeutic agent is added to a molten candy mass. The resultant mixture is then thoroughly mixed to ensure proper distribution of the drug within the molten candy mass. The mixture is then poured into a mold cavity while still molten and allowed to solidify into a solid mass. Alternatively, the hot candy mass may be poured into molds, the size and shape of which may be determined as desired.

For effective application of the drug, the final candy product may contain the drug uniformly distributed throughout in order to ensure uniform levels of medication. Alternatively, for some applications, varying concentrations within known and controlled ranges may be desired to vary the rate of drug administration. Difficulties are encountered in attempting to blend solid drugs in a uniform or otherwise carefully controlled manner. Many drugs are insoluble, or only partially soluble, in one or more of the ingredients of the hard candy base. Thus, the resultant product is often found to be lacking in uniform or controlled distribution of the drug.

In addition, it is often found that when the temperature of the candy mass is increased in order to enable a more uniform distribution (generally to a temperature above approximately 230° C.), considerable decomposition of the drug takes place. While the extent of decomposition may vary, high temperatures are generally undesirable in the handling and processing of medications. Thus, the process of formation of the candy product may itself degrade and/or inactivate the therapeutic agent.

Furthermore, many presently available medicated candy lozenges tend to crumble when placed in the mouth. As a result, uniform release of the drug into the mucosal tissues does not take place. Rather, the crumbled lozenge is mostly chewed, and swallowed, and the drug enters the bloodstream through the stomach and intestines as described above. Thus, it will be appreciated that candy lozenges have very definite limitations for use in the administration of a drug through the oral mucosal tissues. As a result, lozenges have not been used to administer potent, fast-acting drugs, such as drugs that affect the central nervous system, the cardiovascular system, or the renal vascular system.

While the administration of certain drugs through the oral mucosal tissues has shown promise, development of a fully acceptable method for producing a medication in a desirable form and administering the medication has been elusive. It has not been possible to develop an acceptable candy product for use with most drugs without heating the product to the point where degradation will be expected.

It should also be noted that pH conditions within the mouth may tend to adversely affect the administration of certain lipophilic drugs by the mucosal administration route. It has been found in the art that administration of drugs through the mucosal tissues generally occurs best when the drug is in the unionized form. Variations in pH affect the percentage of the drug which is unionized at a particular point in time. As a result, the pH conditions within the mouth often limit the effectiveness of certain drugs administered buccally or sublingually in that those conditions cause the drug to exist in the ionized form which is largely unavailable for transfer across the mucosal tissues.

Other potent drugs are substantially nonlipophilic and do not naturally permeate mucosal tissues. Hence it would be a significant advancement in the art of administering potent, fast-acting drugs, if suitable methods and compositions permitted both lipophilic and nonlipophilic drugs to be administered transmucosally.

It would be another important advancement in the art of administering potent, fast-acting drugs, if suitable methods and compositions provided a precise dosage to a precise effect in every patient. A related advancement in the art would be to provide such methods and compositions that avoid the disadvantages of overdosing, underdosing, and the immediate metabolism encountered in the "first pass effect," yet do not involve injection by needle into the patient.

It would be a further significant advancement in the art to provide methods and compositions for incorporating drugs (including insoluble drugs) into a nondissolvable drug containment matrix which does not require heating the drug to the point that degradation occurs.

Such compositions and methods of manufacture are disclosed and claimed herein.

BRIEF SUMMARY AND OBJECTS OF THE INVENTION

The present invention relates to compositions and methods of manufacture for producing substantially nondissolvable drug containment matrixes for use in administering potent, fast-acting drugs transmucosally. Furthermore, the present invention relates to such compositions and methods which are useful in administering drugs in a dose-to-effect manner such that sufficient drug is administered to produce precisely the desired effect. The invention also relates to a manufacturing technique that enables both lipophilic and nonlipophilic therapeutic agents to be incorporated into a drug containment matrix which may be flavored, if necessary for palatability, and to which an appliance or holder may be attached. In use, the present invention provides for the administration of drugs through the mucosal tissue of the mouth, pharynx, and esophagus, thereby avoiding the problems of both injection and oral administration.

Employing the present invention, the drug may be introduced into the patient's bloodstream almost as fast as through injection, and much faster than using the oral administration route, while avoiding the negative aspects of both methods. A dosage-form within the scope of the present invention can be used to administer drugs in a dose-to-effect manner, or until the precise desired effect is achieved.

The present invention achieves these advantages by incorporating the drug into a nondissolvable drug containment matrix. The drug may be incorporated into a variety of possible nondissolvable containment matrixes. For example, the drug may be incorporated into a sponge-like matrix; the drug may be microencapsulated; the drug may be held within a microsponge; the drug may be contained within a permeable membrane or screen-like barrier; or the drug may be held within other nondissolvable containment vehicles capable of releasing the drug for transmucosal administration.

In those embodiments within the scope of the present invention where the drug is incorporated into a sponge-like matrix, the matrix may be designed to release the drug in response to pressure, either negative or positive, or other similar release trigger. The matrix may be held within a screen or permeable membrane which allows the drug to permeate the screen when exposed to conditions of the mouth, pharynx, or esophagus. Suitable screen-like materials include woven nylon, polypropylene or polyethylene mesh with varying apertures or pore sizes, and porous sheet materials. A suitable screen or membrane preferably is flexible with no (or low) drug absorption or adsorption, free of interaction with physiological tissues such as the oral mucous membrane, palatable in taste and texture, non-irritating, non-toxic, hypoallergenic, and does not leach out plasticizers, such a phthalates.

Alternatively, the sponge-like matrix may be held together with a suitable biocompatible adhesive (either dissolvable or nondissolvable). Typical adhesives include sodium carboxymethylcellulose, sodium alginate, and tragacanth. In other embodiments, the sponge-like matrix may be retained within a compressed powder dosage-form or other dissolvable matrix such as those described in copending patent application Ser. No. 08/82,260, entitled "Compositions and Methods of Manufacture of Oral Dissolvable Medicaments" which is incorporated herein by specific reference.

When the drug is microencapsulated, the microencapsulated drug may be held within a screen or permeable membrane which allows the drug to permeate the screen when exposed to conditions of the mouth, pharynx, or esophagus. The microencapsulated drug may alternatively be held together with a suitable biocompatible adhesive. In addition, in one embodiment within the scope of the present invention, the microencapsulated drug matrix may be retained within a compressed powder dosage-form or other dissolvable matrix as discussed above.

In other possible embodiments of the present invention, the drug (as part of a medicament medium) is contained within a permeable membrane or screen-like barrier. The membrane preferably has a pore size sufficient to permit the drug to pass therethrough. It is important that the drug be retained within the membrane under conditions outside the patient's mouth and that the drug be capable of permeating the membrane within the patient's mouth.

For example, in one preferred embodiment within the scope of the present invention, the medicament medium viscosity is sufficiently high outside the mouth such that the surface tension at the membrane pores prevents the drug from permeating the membrane. But once the dosage-form is placed within the patient's mouth, the viscosity of the medicament medium is lowered so that the drug permeates the membrane. This change in viscosity may be obtained due to salival contact with the medicament medium or due to a higher temperature within the mouth.

In another embodiment within the scope of the present invention, the apparatus includes a drug compartment and a solvent compartment separated by a frangible barrier. In use the barrier is broken and the drug and solvent are mixed, thereby forming a medicament medium. The ability to use drugs in a powdered form improves the shelf-life and stability of the drug.

In yet another embodiment within the scope of the present invention, the drug is capable of permeating the membrane due to pressure effects within the mouth. For instance, negative pressure caused by sucking the dosage-form draws the medicament through the membrane. Alternatively, positive pressure caused by squeezing the dosage-form forces the medicament through the membrane.

The manufacturing methods of the present invention overcome many of the limitations previously encountered in forming a medicated lozenge. The present invention teaches the combination of ingredients by geometric dilution. That is, the two smallest ingredients by weight are first thoroughly mixed, then the next smallest ingredient or ingredients by weight equal to the weight of the previous ingredients is added and is thoroughly mixed with the existing mixture. This procedure is repeated until all of the components, including the desired therapeutic agents, are fully combined.

Another important feature within the scope of the present invention is the ability to use a wide variety of drug forms.

For instance, the active ingredient may be in solid or liquid form, incorporated in microsponges or microencapsulated, captured inside a suitable permeable membrane or bound together with a suitable adhesive.

These embodiments overcome many of the problems of the prior art. According to the present invention, insoluble drugs can be added to the matrix without the necessity of attempting to dissolve the drug. In addition, the high temperatures, which are generally required to form a molten candy matrix and which can cause degradation of some drugs, are avoided using the present invention. Therefore, even drugs with relatively low melting points or those drugs which can experience decomposition below their melting points, can be incorporated into a dissolvable dosage-form.

A further advantage of the present invention is that flavoring problems are overcome in many cases. Flexibility in adding flavors is provided in that solubility of the components is not required in order to incorporate any particular flavor into the matrix. Thus, flavorings, drugs, and other components (which may be insoluble in liquid form) are easily mixed when they exist as a dry powder.

Buffer forming agents and other types of pH control can also be added simultaneously in order to provide for maximum drug efficiency. It will be appreciated that drugs in the unionized form are more readily transported across the mucosal membrane. Therefore, if pH conditions can be adjusted to maximize the percentage of unionized drug available, the effectiveness of the drug is maximized.

Buffering agents are particularly important for those drugs that partially ionize within the pH range of the mouth, such as weak acid and weak base drugs. Generally, buffering agents are more important when hydrophilic drugs are used because those drugs usually have lower mucosal permeability and dissolve more readily in saliva within the mouth.

Permeation enhancers may also be incorporated within the dissolvable matrix to improve the permeability of the mucosal membrane. The permeability of both lipophilic and nonlipophilic drugs may be improved by using suitable permeation enhancers.

It may also be desirable to incorporate a handle or holder the nondissolvable matrix material as the matrix is being formed. Alternatively, the handle may be glued to the matrix material by a bonding agent once the nondissolvable matrix is formed. The handle provides for easy removal of the nondissolvable matrix from the mouth of the patient once the desired effect has been achieved. This is a substantial improvement over existing methods of administering drugs through the mucosal tissues of the mouth.

A number of factors influence the drug administration rate. For instance, incipient solubility, formulation of the drug (microencapsulated, resin, microsponge), buffering agents, pore size and charge (electropotential) on membrane or screen, and the force or vigor with which the patient sucks or squeezes the dosage-form affect the drug administration rate. In addition, the drug solvent (if the drug is in liquid form), i.e., water or oil affects the administration rate.

A drug released from a nondissolvable drug containment matrix within the scope of the present invention and administered through the oral mucosal tissues will quickly enter the patient's bloodstream through the veins which serve these tissues. Appropriate monitoring of the patient's reaction to the drugs which have an observable or monitorable effect (such as a drug affecting the central nervous, cardiovascular, respiratory, or renal vascular systems) will indicate when the drug has evoked a suitable response. The dosage-form may then be removed, or its rate of consumption may be modified in order to maintain the desired effect.

It will be appreciated that the ever present risk of overdosing a patient is substantially minimized through the use of the present invention. According to the present invention, the drug dose is given over a period of time rather than all at once, and the administration rate can be adjusted if it appears to be necessary. Once a sufficient drug response has been achieved, the patient can simply stop sucking or squeezing the dosage-form or the patient or medical professional can easily remove the dosage-form from the patient's mouth.

It is, therefore, a primary object of the present invention to provide methods and compositions for the noninvasive transmucosal administration of a drug to a patient in order to rapidly induce a desired systemic effect.

Another object of the present invention is to provide suitable methods and compositions for the noninvasive transmucosal administration of both lipophilic and nonlipophilic drugs. A related object of the present invention is the use of suitable permeation enhancers which improve drug permeation across the mucosal membrane.

It is a further object of the present invention to provide methods and compositions for administering potent, fast-acting drugs, which administer a precise dosage to obtain a precise effect in every patient. A related object of the present invention is to provide such methods and compositions that avoid the disadvantages of overdosing, underdosing, and the immediate metabolism encountered in the "first pass effect," yet do not involve injection by needle into the patient.

It is yet another object of the present invention to provide methods and compositions for incorporating drugs (including insoluble drugs) into a nondissolvable drug containment matrix which do not require heating the drug to the point that degradation occurs and which permit the use of stable drug forms.

These and other objects and features of the present invention will become more fully apparent from the following description and appended claims taken in conjunction with the accompanying drawings.

BRIEF DESCRIPTION OF THE DRAWINGS

FIG. 5 is a perspective view of still another dosage-form within the scope of the present invention including a nondissolvable fibrous covering embedded with medicament.

FIG. 6 is a cross-sectional view of the embodiment illustrated in FIG. 5 taken along line 6—6 of FIG. 5.

FIG. 7 is a perspective view of another embodiment within the scope of the present invention wherein the medicament administration rate may be adjusted by altering the pressure within the medicament chamber.

DETAILED DESCRIPTION OF THE PREFERRED EMBODIMENTS

1. General Discussion

The present invention is related to methods of manufacture and compositions which facilitate the oral transmucosal delivery of a medication. Simply stated, the present invention relates to a dosage-form, or similar type of composition, which contains a therapeutic drug. The dosage-form includes a nondissolvable drug containment matrix or vehicle capable of releasing the drug for administration through the oral mucosal tissues. The drug is delivered to the patient through the mucosal tissues of the mouth, pharynx, and esophagus as the patient sucks or squeezes on the drug-containing dosage-form.

This particular method of delivery overcomes several of the limitations encountered in the delivery of drugs either orally or by injection. One of the primary advantages of the present invention is the ability to introduce drugs to a patient in a "dose-to-effect" manner. The drug is given to the patient until the precisely desired effect is obtained; this is in distinction to prior art methods where a predetermined quantity of the drug is introduced to the patient. Once the desired effect is obtained, the patient or the medical professional simply removes the dosage-form from the patient's mouth.

The present invention achieves these advantages by incorporating the drug or therapeutic agent into a nondissolvable drug containment matrix. The drug may be incorporated into a variety of possible nondissolvable containment matrixes. For example, the drug may be incorporated into a sponge-like matrix; the drug may be microencapsulated; the drug may be held within a microsponge; the drug may be contained within a permeable membrane or screen-like barrier; or the drug may be held within other nondissolvable containment vehicles capable of releasing the drug for transmucosal administration.

Figure 1A:
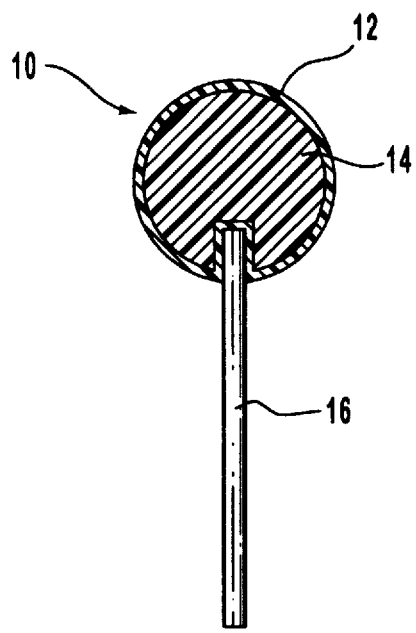
FIG. 1A is a cross-sectional view of a dosage-form within the scope of the present invention including a medicament medium within a permeable membrane barrier.
Figure 1B:
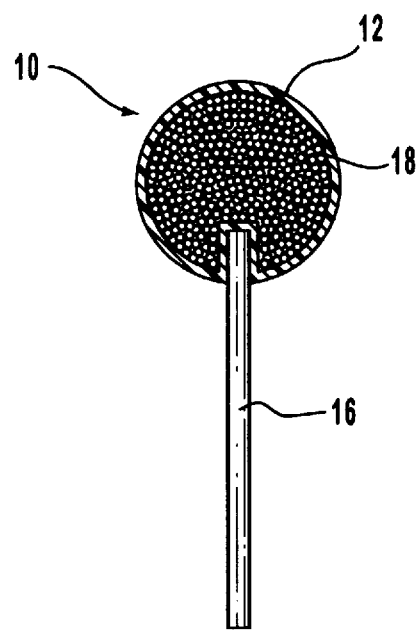
FIG. 1B is a cross-sectional view of a dosage-form within the scope of the present invention including a plurality of microencapsulated drug particles within a permeable membrane barrier.
Figure 1C:
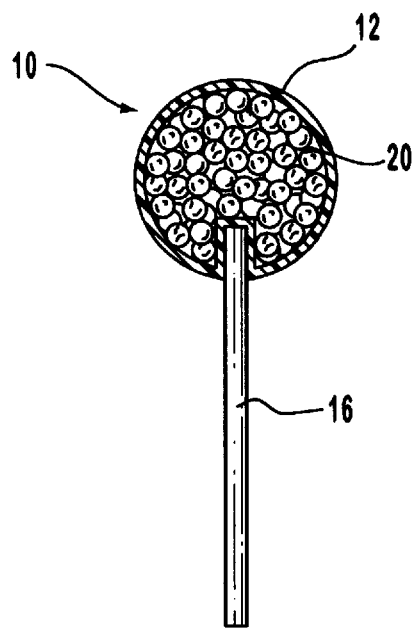
FIG. 1C is a cross-sectional view of a dosage-form within the scope of the present invention including a plurality of drug-containing microsponges within a permeable membrane barrier.

Reference is made to FIGS. 1A–1C which illustrate various dosage-forms within the scope of the present invention having a permeable membrane or screen-like barrier which retains the drug containing vehicle.

Dosage-form 10, shown in FIG. 1A, includes a permeable barrier 12 which retains a quantity of medicament medium 14. A handle 16 is preferably secured to the dosage-form to facilitate insertion, removal, and proper placement of the dosage-form in the patient's mouth. Barrier 12 may be screen-like with relatively large pores or membrane-like with relatively small pores. The barrier preferably has a pore size sufficient to permit the drug to pass therethrough. It is important that the drug be retained within the barrier under conditions outside the patient's mouth and that the drug be capable of permeating the barrier within the patient's mouth.

For example, in one preferred embodiment within the scope of the present invention, the medicament medium viscosity is sufficiently high outside the mouth such that the surface tension at the barrier pores prevents the drug from permeating the barrier. But once the dosage-form is placed within the patient's mouth the viscosity of the medicament medium is lowered so that the drug permeates the barrier. In one embodiment the viscosity of the medicament medium is lower within the mouth due to salival contact with the medicament medium. In other embodiments the viscosity of the medicament medium is lower within the mouth due to an increased temperature within the mouth.

In another embodiment within the scope of the present invention, the drug within medicament medium 14 permeates the barrier in response to pressure effects within the mouth. For instance, negative pressure caused by sucking the dosage-form draws the medicament through the barrier. Alternatively, positive pressure caused by squeezing the dosage-form forces the medicament through the barrier.

Referring now to FIG. 1B, dosage-form 10 is similar to the dosage-form of FIG. 1A except that a plurality of microencapsulated drug particles 18 are retained within permeable barrier 12. A handle 16 is also preferably secured to the dosage-form to facilitate insertion, removal, and proper placement of the dosage-form in the patient's mouth. Barrier 12 may be screen-like with relatively large pores or membrane-like with relatively small pores. The barrier preferably has a pore size sufficient to permit the drug to pass therethrough while retaining the microencapsulated drug particles within barrier 12.

Microencapsulated drugs are drug particles or droplets which have been coated with a protective coating material. Typical coating materials include fats, waxes, triglycerides, fatty acids, fatty alcohols, ethoxylated fatty acids and alcohols, stearates, sugars, poly(ethylene glycol), certain metals, gums, hydrocolloids, latexes, and various polymer-based formulations such as polyethylene, ethyl cellulose, ethylene-vinyl acetate, ethylene-acrylic acid, polyamides, and some enteric polymers.

The protective coating material of microencapsulated drugs prevents drug degradation by moisture, retards oxidation of the drug, decreases evaporation and sublimation, protects the drug from reaction with other ingredients, and masks unpleasant taste of some drugs. Drug microencapsulation techniques are known in the art.

FIG. 1C illustrates a dosage-form 10 similar to that illustrated in FIG. 1B except that a plurality of drug-containing sponge-like matrixes 20 are retained within barrier 12. Sponge-like matrixes, which include microsponges, are devices capable of entrapping a medicament and then releasing the medicament over time. These sponge-like matrixes are biologically inert, non-irritating, non-mutagenic, non-allergenic, non-toxic, and non-biodegradable. They can even improve medicament stability. Suitable microsponges or sponge-like matrixes are known in the art.

Like true sponges, the sponge-like matrixes or microsponges contain a myriad of interconnecting voids within a non-collapsible structure with a large porous surface. The size of the sponge-like matrix as well of the number and size of the internal pore structure can be varied depending on the medicament size and viscosity.

The medicament is released from a sponge-like matrix in response to a suitable "trigger". For example, rubbing or pressing the sponge-like matrix, elevating the temperature of the matrix (as within the patient's mouth vis-a-vis ambient temperature), or introducing suitable solvents such as saliva can cause a controlled release of the medicament. Pressure may also be used to release the drug from the sponge-like matrixes. Squeezing and sucking a dosage-form containing the sponge-like matrixes saturated with the medicament will release the medicament.

In the embodiments within the scope of the present invention shown in FIG. 1C where the drug is incorporated into a sponge-like matrix, the matrix may be held within barrier 12 which allows the drug to permeate the barrier when exposed to a suitable trigger.

Figure 2A:
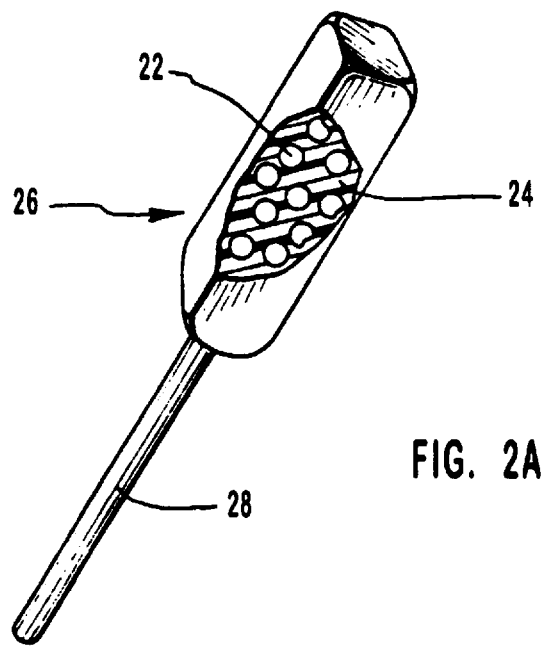
FIG. 2A is a perspective view which is partially cut away of a dosage-form within the scope of the present invention including a plurality of drug-containing microsponges bound together with a binding material.

In other embodiments within the scope of the present invention, the sponge-like matrix or microencapsulated drug particles may be held together with a biocompatible binding material or adhesive (either dissolvable or nondissolvable) such as sodium carboxymethylcellulose, sodium alginate, and tragacanth. An example of one such embodiment is illustrated in FIG. 2A. A plurality of microsponge 22 are bound together in a dosage-form 24 with binding material 26. A handle 28 is preferably attached to the dosage form to facilitate insertion, removal, and proper placement of the dosage-form in the patient's mouth.

Although FIG. 2A illustrates a plurality of microsponges bound together by a binding material in a dosage-form, it will be appreciated that other drug containing vehicles, such as microencapsulated drug particles, may also be suitably bound together with a binding material.

In yet another embodiment of the present invention, the sponge-like matrix or microencapsulated drug particles may be retained within a compressed powder dosage-form or other dissolvable matrix such as those described in copending patent application Ser. No. 07/403,751 filed Sep. 4, 1989 in the names of THEODORE H. STANLEY and BRIAN HAGUE, and entitled "Compositions and Methods of Manufacture of Oral Dissolvable Medicaments" which is incorporated herein by specific reference.

Figure 2B:
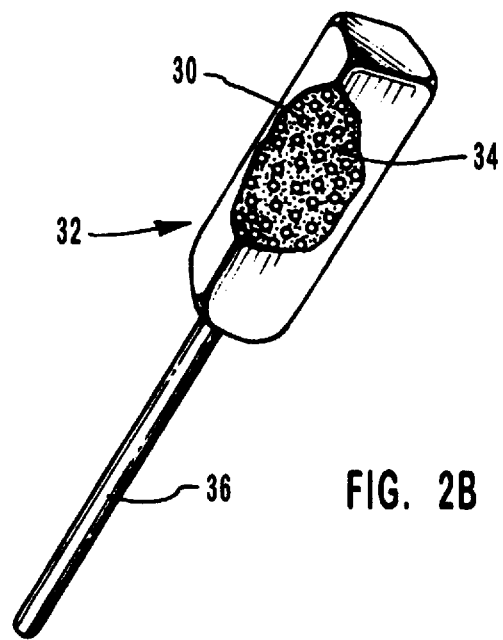
FIG. 2B is a perspective view which is partially cut away of a dosage-form within the scope of the present invention including a plurality microencapsulated drug particles bound together with a binding material.

In the embodiment illustrated in FIG. 2B, a plurality of microencapsulated drug particles 30 are compressed together in a dosage-form 32 with compressible sugar 34 and other ingredients described in the copending patent application identified-above. A handle 36 is also preferably attached to the dosage-form. Although FIG. 2B illustrates microencapsulated drug particles retained within a compressed powder dosage-form, it will be appreciated that other drug containing vehicles, such as microsponges, may also be suitably retained within dosage-forms made from dissolvable matrix materials described above.

From the foregoing, the nondissolvable matrix compositions are preferably attached to a holder or handle. Attaching the nondissolvable matrix to a holder facilitates the administering of precise dosages. Once a particular effect is induced, the dosage-form can be withdrawn using the holder as described above. The holder may be attached to the nondissolvable matrix by incorporating the holder into the nondissolvable matrix as the dosage-form is being formed.

Alternatively, the holder may be glued, compressed, screwed, snapped, or otherwise attached to the nondissolvable matrix once the matrix is formed. In yet other embodiments, dosage-forms may be assembled immediately prior to use by sliding nondissolvable connectable dosage elements containing a suitable medicament onto an appropriately configured holder. Optionally dissolvable or nondissolvable flavored connectable elements may also be slid onto the holder.

Figure 3:
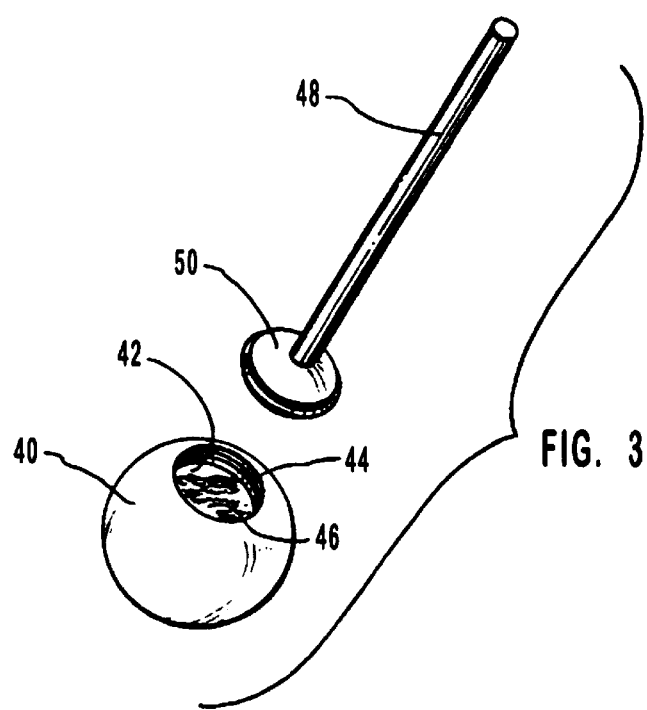
FIG. 3 is a perspective view of another dosage-form embodiment within the scope of the present invention having a removable handle.

In one embodiment illustrated in FIG. 3, a permeable barrier 40 defines a chamber 42 and an opening 44 to the chamber. The chamber is filled with a drug composition 46 in the form of microsponges, microencapsulated drug particles, a medicament medium, or other similar drug-containing formulation. A holder 48 includes a cover 50 for opening 44. Cover 50 is configured to securely seal opening 44 while at the same time provide means for attaching holder 48 to the dosage-form. In this way, the quantity and concentration of drug may be placed within the dosage-form prior to use. The drug may even be replenished or replaced during use if necessary.

It will be appreciated that attachment of the drug containing matrix onto a holder can facilitate the transmucosal absorption of a variety of therapeutic agents. Attachment to a holder also facilitates verifiable transfer of the medication to the patient. For instance, the medication may be bound to a dye such that loss of color indicates transfer of the medication to the patient. The holder permits the drug-containment matrix to be positioned at the desired location within the patient's mouth and provides a convenient point of reference enabling the medical professional to verify the proper placement of the matrix.

Figure 4:
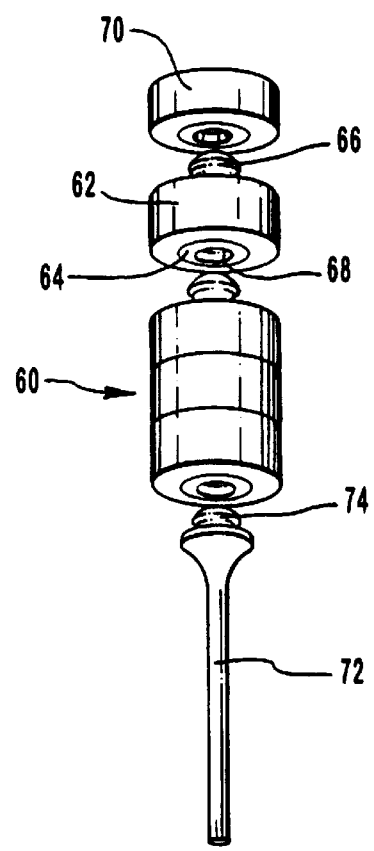
FIG. 4 is a perspective view of yet another dosage-form within the scope of the present invention utilizing connectable dosage elements.

Dosage-form 60, illustrated in FIG. 4, contains a plurality of connectable dosage elements 62. Dosage elements 62 include a solid core 64 defining a male coupling 66 and a female coupling 68. A dosage cap 70 is configured substantially the same as dosage elements 62, except that the solid core does not define a male coupling. The dosage elements are preferably constructed of a screen-like material such as woven fabric or a perforated sheet of material which is molded or fabricated around the solid core. The solid core may be constructed of a suitable biocompatible material such as polyethylene. The screen-like material defines a chamber for holding the desired medicament and releases the medicament in substantially the same manner as described above in connection with FIGS. 1A–1C.

Dosage-form 60 is constructed by interlocking a plurality of dosage elements through their respective male and female couplings. A holder 72 which includes a male coupling 74 constructed at one end thereof is preferably coupled to the connectable dosage elements. The ability to assemble a dosage-form prior to use permits the dosage-form to be "customized" to the individual patient or circumstances. Various concentrations of a drug, or even multiple drugs may be administered in this manner.

FIGS. 5 and 6 illustrate another possible dosage-form embodiment within the scope of the present invention. Dosage-form 80 includes a covering material 82 molded around a semisolid core 84. The semisolid core is preferably mounted to a holder 86. Covering material 82 is preferably a thick mesh or perforated sheet having the desired medicament 88 embedded therein which will permit the medicament to leach out or otherwise enter the patient's mucosal membrane. The medicament may be powdered, liquid, microencapsulated, or otherwise trapped in the covering material 82 so that the medicament will be released within the oral environment.

Figure 8:
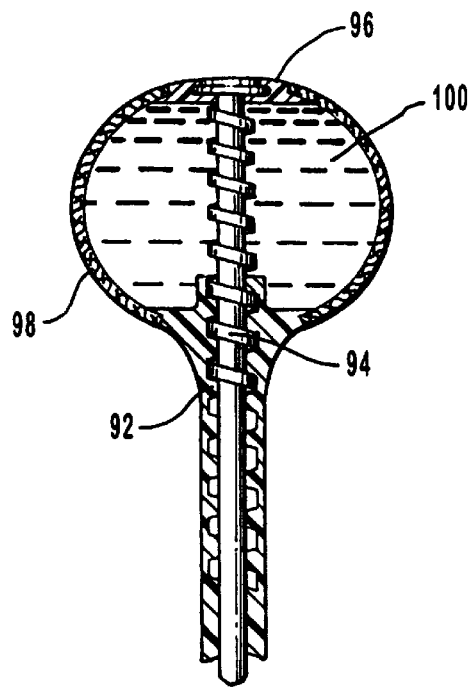
FIG. 8 is a cross-sectional view of the embodiment illustrated in FIG. 7 taken along line 8—8 of FIG. 7.
Figure 9:
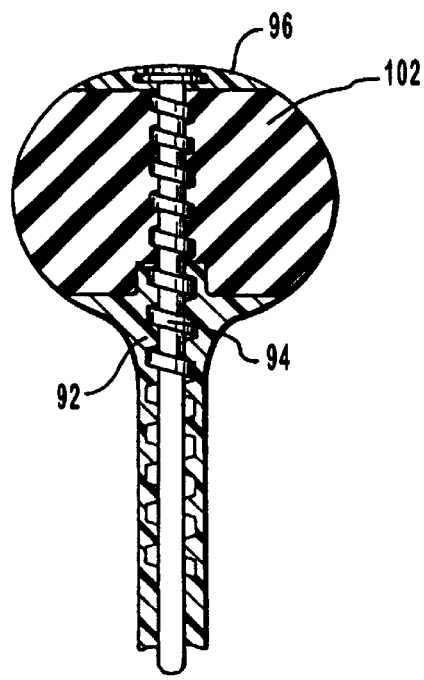
FIG. 9 is a cross-sectional view of an alternative embodiment within the scope of the present invention applying the concepts disclosed in FIG. 7.

The embodiments illustrated in FIGS. 7–9 permit the drug administration rate to be controlled by adjusting the pressure applied to a medicament medium. Dosage-form 90 shown in FIGS. 7 and 8 includes a holder 92 and a screw 94 internally threaded within holder 92. Secured to holder 92 and to screw cap 96 is a semipermeable membrane 98 which provides a containment barrier for a quantity of medicament medium 100. Membrane 98 is similar to those described above by having a pore size sufficient to permit medicament to pass therethrough within an oral environment. The medicament medium may be a liquid medicament solution or a suspension.

In operation, dosage-form 90 is placed within the patient's mouth and screw 94 is twisted such that medicament medium 100 is placed under pressure thereby increasing the rate the medicament permeates membrane 98.

The embodiment illustrated in FIG. 9 is similar to that shown in FIGS. 7 and 8 except that the medicament is embedded within a semisolid medicament medium 102 embedded with medicament which is capable of being compressed. In operation, the dosage-form is placed within the patient's mouth and screw 94 is twisted such that medicament medium 102 is compressed thereby directly releasing the medicament for absorption across the patient's mucosal membrane.

Figure 10:
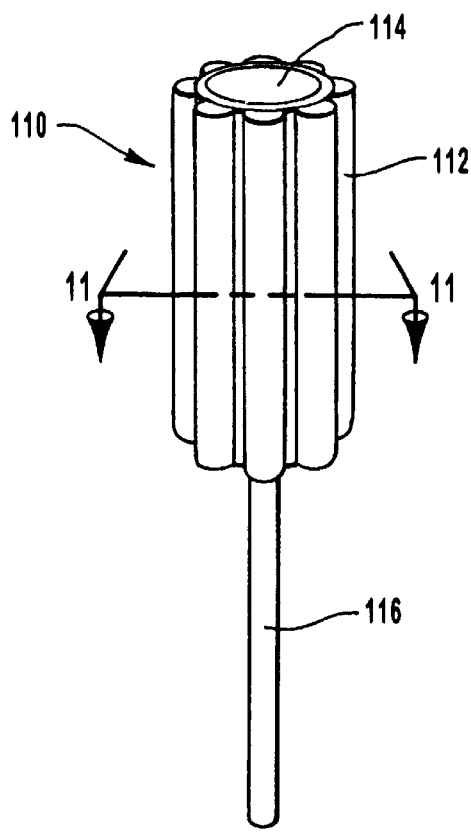
FIG. 10 is a perspective view of another possible dosage-form embodiment within the scope of the present invention having a plurality of longitudinal tube-like members containing medicament.
Figure 11:
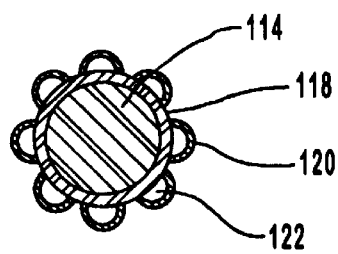
FIG. 11 is a cross-sectional view of the embodiment illustrated in FIG. 10 taken along line 11 of FIG. 10.

FIGS. 10 and 11 show yet another possible embodiment within the scope of the present invention. Dosage-form 110 includes a plurality of tube-like members 112 located around the periphery of a semisolid core 114. The semisolid core is preferably mounted to a holder 116. A layer of expandable material 118 may optionally be located between the tube-like members and the semisolid core.

The tube-like members are formed from a screen-like material 120, such as nylon or dacron mesh, which is molded in a semicylindrical shape. The tube-like members are mounted to expandable material 118 such that the screen-like material provides a barrier for a quantity of medicament 122. Expandable material 118 is preferably constructed of methylcellulose or similar material encased in a porous mesh which will hydrate and expand when placed in the patient's mouth. Upon expansion, increased pressure is exerted on the porous tube-like members, thereby increasing the rate medicament is released from the dosage-form.

Figure 12:
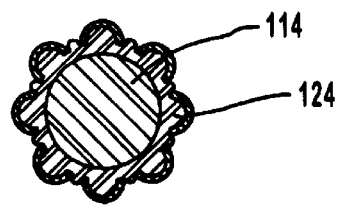
FIG. 12 is a cross-sectional view of an alternative embodiment within the scope of the present invention applying the concepts disclosed in FIG. 10.

The embodiment illustrated in FIG. 12 is similar to that shown in FIGS. 10 and 11, except that the medicament is embedded directly within the an expandable material 124 such as methylcellulose. The medicament is released as material 124 expands within the patient's mouth.

Another optional embodiment which is not shown in the figures replaces semisolid core 114 with a hollow tube constructed of polyethylene or similar material which can be injected with air such that it expands against the tube-like members containing the medicament. The pressure (from a known volume of injected air) and the pore size covering the tube-like members governs the delivery rate of the medicament.

Figure 13:
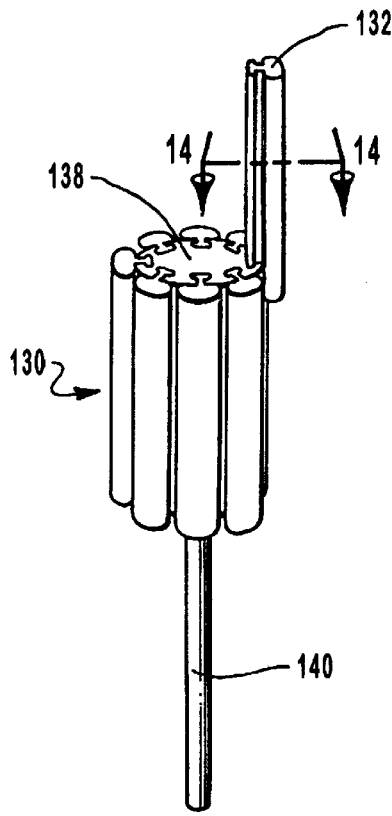
FIG. 13 is a perspective view or yet another variation of the embodiment illustrated in FIG. 10 having a plurality of removable tube-like members which contain medicament.
Figure 14:
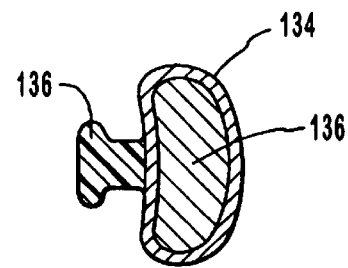
FIG. 14 is a cross-sectional view of a tube-like member illustrated in FIG. 13 taken along line 14—14 of FIG. 13.

FIGS. 13 and 14 show a dosage-form which is a variation of the embodiment illustrated in FIG. 10. Dosage-form 130 of FIGS. 13 and 14 includes a plurality of tube-like members 132. Tube-like members 132 are shown in cross-section in FIG. 14. Members 132 include a screen-like material 134 which encapsulates a quantity of medicament medium 136. A rigid stem 138 is attached to screen-like material 134 and is configured to be slid and locked into corresponding slots formed in a solid core 138. A handle 140 is preferably secured to the solid core to facilitate placement and removal of the dosage-form.

Dosage-form 130 may be assembled prior to use by sliding the rigid stems of a plurality of tube-like members 132 into corresponding slots formed in the solid core. The ability to assemble a dosage-form prior to use permits the dosage-form to be "customized" to the individual patient or circumstances. Various concentrations of a drug, or even multiple drugs may be administered in this manner.

Figure 15:
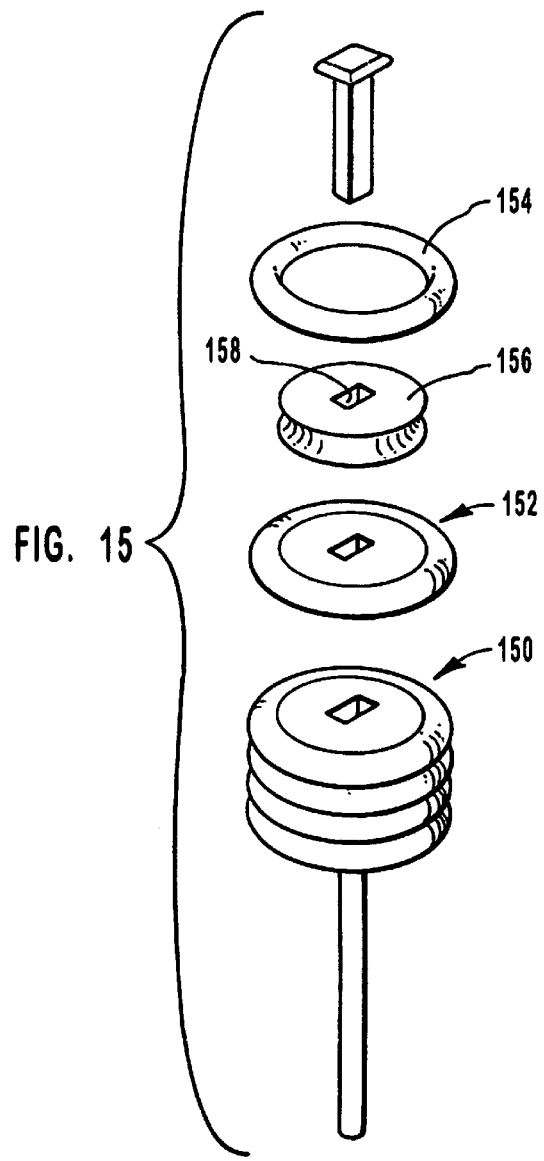
FIG. 15 is a perspective exploded view of another embodiment applying the principles of the present invention having a plurality of ring-shaped dosage members which may be assembled to form a complete dosage-form.

FIG. 15 illustrates another possible dosage-form embodiment which may be individually assembled prior to use. Dosage-form 150 of FIG. 15 is assembled from a plurality of dosage elements 152. Each dosage element includes a ring 154 which is positioned around a semisolid disk 156. Rings 154 are fabricated from appropriate porous material such as woven nylon or dacron or sheets of perforated nylon, polypropylene, or polyethylene. Rings 154 are filled with medicament, either liquid or powder. The semisolid disks define a hole 158 therein such that a plurality of dosage elements may be assembled on a holder similar to dosage-forms described in patent application Ser. No. 07/060,045. The ability to assemble a dosage-form 150 prior to use permits the dosage-form to be "customized" to the individual patient or circumstances. Various concentrations of a drug, or even multiple drugs, may be administered in this manner.

The foregoing dosage-forms are given to illustrate various embodiments which may be made in accordance with the present invention. It is to be understood that the foregoing dosage-form configurations are not comprehensive or exhaustive of the many types of embodiments of the present invention. It is important that the nondissolvable dosage-form configuration be biocompatible and capable of releasing the drug for absorption through the patient's mucosal tissues. The configuration should preferably have a structure, shape, and texture which is palatable to the patient.

Localization of effects by some therapeutic agents such as local anesthetic agents, antiplaque agents, local antipruritic agents, local antisecretory agents, and local antifungal agents can also be accomplished according to the present invention. Immediate systemic effects from central nervous system-acting drugs (such as sedation, anxiolysis, analgesia, amnesia, and anesthesia), cardiovascular-acting agents (such as antihypertensives and antianginal drugs), renal vascular-acting agents, and numerous other therapeutic agents can also be accomplished by employing the present invention.

Placing a drug dosage-form onto a holder also facilitates the temporary removal of medication for inspection or the reduction of the effect when necessary. Unlike administration of drugs orally or even sublingually, the present composition can easily be removed to assess the effect induced at any particular time. When a pill or lozenge is used, removal from the patient's mouth at an intermediate stage to assess effect is generally impractical, if not impossible.

Nondissolvable drug-containment matrixes attached to a holder can also avoid aspiration of the dosage-form in contrast to a lozenge. One major problem with existing lozenges and the like is their tendency to crumble. Once the lozenge crumbles, controlled transmucosal delivery is less ideal.

The present invention provides the capability of providing a palatable medication. With many drugs, it has previously been extremely difficult to provide a good tasting medicine because of the extreme bitterness or other unpleasant taste of many drugs. The use of microencapsulation and microsponge technologies tends to mask the unpleasant taste of many drugs. In addition, favorable taste characteristics can be accomplished by adding various flavors, sweeteners, and the like to form an ideal mix of products. Since the components are combined as solids or liquids (or even liquids that are slowly released from microsponges), problems associated with combining flavoring components insoluble in a molten candy mass are avoided.

It is important to note that it is possible, according to the present invention, to use the free acid or free base form of certain drugs and to buffer those drugs such that extremes in pH, and resulting bad taste, are avoided.

Another important feature of the present invention is the incorporation of permeation enhancers within the nondissolvable matrix. The permeation enhancers improve the mucosal membrane permeability to lipophilic and nonlipophilic drugs. Thus, the compositions and methods within the scope of the present invention permit the use of lipophilic as well as nonlipophilic drugs.

2. Methods of Manufacture

In order to prepare a nondissolvable drug containment matrix for formation into a dosage-form within the scope of the present invention, the drug is placed within a drug containment vehicle or matrix. There are three presently preferred drug containment vehicles: (1) a sponge-like vehicle or microsponge, (2) microencapsulation, and (3) a permeable membrane or screen-like barrier for retaining a medicament medium. In all three of the foregoing general embodiments other components may be added to improve the effectiveness and acceptance of the resultant dosage-form.

The types of components involved generally fall into the following categories:

(1) flavorings,
(2) sweeteners,
(3) flavor enhancers,
(4) buffer forming agents,
(5) one or more therapeutic agents, and
(6) permeation enhancers.

The components may be a releasable or slowly releasable liquid ingredient of the medicament medium or the components may be incorporated within a sponge-like matrix or microencapsulated. All the incipients or inactive ingredients should be on the GRAS list ("generally regarded as safe").

A wide range of flavors are available for preparing good tasting and desirable medications within the scope of the present invention. These are required in order to mask the unpleasant taste of the drug. Flavorings may be combined, as desired, to produce a particular flavor mix which is compatible with a particular medication. Some of the confectioner's flavorings which have been used in the context of the present invention include artificial vanilla, vanilla cream, mint, cherry, spearmint, grape, coconut, chocolate, menthol, licorice, lemon, and butterscotch.

Other flavorings known in the confectionery arts may also be acceptable because of the ease of combining the ingredients of the present invention. Any number of flavorings may be combined in any desired ratio in order to produce the specific desired taste characteristics required for any particular application. For example, flavor combinations may be varied in order to be compatible with the flavor characteristics of any specific drug.

In order to produce a desirable color for the end product, artificial colorings may also be added to the composition. The flavorings described above are generally a white powder, as are the other major components. Therefore, additional coloring is necessary if a colored end product is desired. Coloring may also be important as a code to indicate the type and concentration of drug contained within a particular dissolvable matrix. Any type of color known to be "FD&C" certified, may be used to provide coloring to the product.

In order to provide a good tasting medication, sweeteners are preferably added to the composition. Sweeteners which are presently preferred include aspartame (NutraSweet®) and compressible confectioner's sugar. Other sweeteners, such as fructose and sorbitol, mannitol, xylitol, cyclamates, acesulfame K, thaumatin, sucralose, alitame, PS99/PS100, glycyrrhizin, monellin, stevioside, miraculin, or L-sugars may also be acceptable for use within the scope of the present invention. Again, it is desired that a sweetener or combination of sweeteners be obtained which is compatible with the drug and the other components such that a good tasting dosage-form is produced.

Maltodextrin and cyclodextran may also be added to provide a better tasting composition. Maltodextrin and cyclodextran are generally employed in order to dissipate unpleasant flavors (such as the bitter taste of most drugs) within the composition.

For some applications, it may be desirable to add a flavor enhancer to the composition in order to achieve a good tasting product. Flavor enhancers provide a more pleasant sensation in the patient's mouth during consumption of the dosage-form. Flavor enhancers within the scope of the present invention include materials such as ribotide (a nucleotide) and monosodium glutamate ("msg").

Appropriate changes in flavoring ingredients can be made to mask or optimize flavor perception in order to achieve ultimate acceptance of the dosage-form by the desired patient group, be it adult, juvenile, pediatric, or neonate.

As will be discussed in more detail below, it may also be desirable to include buffering agents within the composition. Buffering agents provide the ability to place the medication in the mouth in a favorable pH environment for passage across the mucosal tissues of the mouth, pharynx, and esophagus. Buffering agents incorporated within the composition can be used to affect a pH change in the salival environment of the mouth in order to favor the existence of a unionized form of the active ingredient or drug which more readily moves through the mucosal tissues.

In addition, appropriate pH adjustment can aid in producing a more palatable product with drugs which are either severely acidic (and thus sour) or severely basic (and thus bitter). As a result, a buffer system such as citric acid/sodium citrate has been found to be desirable for addition into the dissolvable matrix. A phosphate buffer system may also be used.

A suitable permeation enhancer capable of improving the drug permeability across the mucosal membrane may also be included in the dissolvable composition. Permeation enhancers are particularly important when nonlipophilic drugs are used, but may be valuable for lipophilic drugs as well. Examples of typical permeation enhancers which may be used within the scope of the present invention are discussed below.

Added to the nondissolvable drug containment matrix described above will be the appropriate therapeutic agent or drug. As will be discussed in more detail below, various types of drugs are easily incorporated into the matrix compositions of the present invention. Typical drugs used within the scope of the present invention include agents which affect the central nervous, the cardiovascular, respiratory, renal vascular, or other body system.

3. Control of pH in View of Drug pKa

It is well known that most drugs are weak acids or weak bases and are present in solution in both the unionized and ionized forms. It has been found that the unionized portion of the drug is usually lipid soluble and can readily diffuse across the cell membrane. The ionized portion, conversely, is often lipid insoluble and in some instances, may not effectively penetrate the lipid membrane of the cell. As a result, drugs in the ionized form are generally inefficient in producing a drug effect on the central nervous, cardiovascular, and renal vascular systems.

Whether a drug exists in the ionized or unionized form is largely dependent upon its pKa, and correspondingly on the pH of the solution. The present invention provides the unique ability to control the pH of the solution and thus the ratio of unionized to ionized form of the drug.

Ingredients of the nondissolvable drug containment matrix or dosage-form can be designed to impart sufficient change in the pH of the saliva within the mouth such that the concentration of the unionized drug is increased. When the percentage of unionized drug is increased, transmucosal absorption of the drug is correspondingly increased. Therefore, by influencing the salival pH environment, it is possible to greatly improve the extent and rapidity of actual drug absorption, and therefore, the initial onset of the effect of the drug. Adding pH buffering systems (such as phosphate or citrate buffer systems) into the dosage-form can greatly facilitate delivery of the drug in the unionized (lipid soluble) form.

It is often desirable for the pKa to range from approximately 5 to approximately 8 in order to maximize drug delivery. pKa is defined as the negative logarithm (base 10) of the dissociation constant (Ka). pKa may also be defined as the pH at which a given acid is 50% ionized and 50% unionized. The term pKb is used when referring to a base. pKa and pKb can be calculated from the pH using the well-known Henderson-Hasselbach equation if concentrations of the charged and uncharged species are known. The Henderson-Hasselbach equation is as follows:

$$pKb = pH + \log\left|\frac{charged}{uncharged}\right| \text{ for bases}$$

$$pKa = pH + \log\left|\frac{uncharged}{charged}\right| \text{ for acids}$$

From these equations, the unionized portion of the drug will be increased by lowering the pH for weak acid drugs and increasing the pH for weak base drugs.

The effect on the pKa of varying pH, and thus on the unionized drug available, is extremely dramatic. For example, sodium methohexital (the salt of a weak acid), a potent central nervous system-acting drug, has a pKa of 7.9. If at the same time the general pH of the saliva is about 7.5, these values can then be placed in the Henderson-Hasselbach equation as follows:

$$7.9 = 7.5 + \log(X)$$

where X is the ratio of the unionized to the ionized drug form. Solving this calculation indicates that under typical conditions in the mouth, 72% of the methohexital available would exist in the unionized form. As was mentioned above, the unionized drug form is the primary form that is transported across the lipid cell membrane.

In the event that the salival pH is buffered down to approximately 6.7, the ratio of unionized to ionized drug changes dramatically. This results in a corresponding dramatic change in the amount of drug available. Under these conditions, 94% of the drug available exists in the unionized form.

Comparing the ratio of unionized to ionized drug produced under the two sets of pH conditions described above, it can be seen that dramatic changes occur. Changing the pH from 7.5 to 6.7 produces a substantial improvement in the concentration of unionized drug available for delivery across the lipid membrane. This results directly in a dramatic improvement in drug delivery across the cell membranes in the mouth and a corresponding increase in the effectiveness of the drug administered.

Changes in pH such as those discussed above can be accomplished by incorporating particular buffer systems within the dosage-form composition. One presently preferred buffer system is a citric acid/sodium citrate system; however, other conventional buffers (such as phosphate) may also be used. By using such a buffer, dramatically better results may be achieved such that oral transmucosal drug absorption is a fully feasible and optimal delivery method.

It will be appreciated that an additional advantage of the change of the pH may be that the taste characteristics of the drug can be improved. Drugs which are very high in pH typically are very bitter in taste. As the pH drops, the taste becomes less bitter, then salty, and may eventually become sour. Flavorings can more adequately improve the taste characteristics of drugs in the lower pH ranges. As a result, in addition to improving the drug delivery, buffering pH nay also improve the taste characteristics of the composition.

It will be appreciated that an additional advantage of the change of the pH may be that the taste characteristics of the drug can be improved. Drugs which are very high in pH typically are very bitter in taste. As the pH drops, the taste becomes less bitter, then salty, and may eventually become sour. Flavorings can more adequately improve the taste characteristics of drugs in the lower pH ranges. As a result, in addition to improving the drug delivery, buffering pH may also improve the taste characteristics of the composition.

Although the foregoing discussion has focused on the alteration of pH to enhance drug permeability by increasing the percentage of unionized drug forms, pH may enhance drug permeability by unknown mechanisms. For example, pH may affect drug molecular configuration which enhances drug permeability. Nonetheless, drug pH is often an important consideration in drug administration.

4. Mucosal Membrane Permeation Enhancers

As discussed above, most drugs are present in solution in both the unionized and ionized forms. Generally only lipid soluble or lipophilic drugs readily diffuse across mucosal membranes. However, it has been found that nonlipophilic drugs may diffuse across mucosal membranes if the mucosal membrane is treated with a permeation enhancer. It has also been found that certain permeability enhancers can significantly enhance the permeability of lipophilic and nonlipophilic drugs.

Typical permeation enhancers include bile salts such as sodium cholate, sodium glycocholate, sodium glycodeoxycholate, taurodeoxycholate, sodium deoxycholate, sodium lithocholate chenocholate, chenodeoxycholate, ursocholate, ursodeoxycholate, hyodeoxycholate, dehydrocholate, glycochenocholate, taurochenocholate, and taurochenodeoxycholate. Other permeation enhancers such as sodium dodecyl sulfate ("SDS"), dimethyl sulfoxide ("DMSO"), sodium lauryl sulfate, salts and other derivatives of saturated and unsaturated fatty acids, surfactants, bile salt analogs, derivatives of bile salts, or such synthetic permeation enhancers as described in U.S. Pat. No. 4,746,508 may also be used.

It is almost impossible to predict which enhancer will work best for a given drug. For each individual drug, only experiments can tell which enhancer is the most suitable. However, it is generally believed that bile salts are good enhancers for hydrophilic drugs and long chain fatty acids, their salts, derivatives, and analogs are more suitable for lipophilic drugs. DMSO, SDS, and medium chain fatty acids (C-8 to about C-14), their salts, derivatives, and analogs may work for both hydrophilic and lipophilic drugs.

The effectiveness of some enhancers may vary depending on the chemical compound to be permeated. One particular enhancer may work very well on one drug but may not have any effect on another drug. For example, oleic acid greatly improves the transdermal permeability of estradiol, a very lipophilic drug, but oleic acid does not have any effect on the transmucosal permeability of glucose, a very hydrophilic drug. Although it is possible to speculate whether a given enhancer may or may not enhance a given drug's permeability, the actual effectiveness of an enhancer should be verified experimentally.

The permeation enhancer concentration within the dissolvable matrix material may be varied depending on the potency of the enhancer and rate of dissolution of the dissolvable matrix. Other criteria for determining the enhancer concentration include the potency of the drug and the desired lag time. The upper limit for enhancer concentration is set by toxic effect to or irritation limits of the mucosal membrane.

The following is a list of typical enhancers and an exemplary concentration range for each enhancer:

| Enhancer | Operational Concentration | Preferred Range |
| --- | --- | --- |
| sodium cholate | 0.02%–50% | 0.1%–16% |
| sodium dodecyl sulfate | 0.02%–50% | 0.1%–2% |
| sodium deoxycholate | 0.02%–50% | 0.1%–16% |
| taurodeoxycholate | 0.02%–solubility | 0.1%–16% |
| sodium glycocholate | 0.02%–solubility | 0.1%–16% |
| sodium taurocholate | 0.02%–solubility | 0.1%–16% |
| DMSO | 0.02%–solubility | 5%–50% |

5. Suitable Therapeutic Agents

In order for the present invention to operate effectively, it is necessary that the therapeutic agent incorporated within the nondissolvable drug containment matrix be capable of permeating the mucosal membrane either alone or by suitable adjustments in the environmental pH, or other chemical modification or in combination with a suitable permeation enhancer.

The present invention has applicability to a variety of drugs affecting the central nervous system. For example, the present invention may easily be utilized in the administration of opioid agonists (such as fentanyl, alfentanil, sufentanil, lofentanil, and carfentanil), opioid antagonists (such as naloxone and nalbuphene), butyrophenones (such as droperidol and haloperidol); benzodiazepines (such as valium, midazolam, triazolam, oxazolam, and lorazepam); GABA stimulators (such as etomidate); barbiturates (such as thiopental, methohexital, thiamazol, pentobarbital, and hexobarbital); di-isopropyl-phenols drugs (such as diprivan); and other central nervous system-acting drugs such as levodopa. It will be appreciated that other drugs may also be utilized within the scope of the present invention either singly or in combination.

Table 1 lists some of the CNS-acting drugs which are suitable for incorporation into the dosage-form of the present invention, as well as some of the characteristics of those drugs.

TABLE 1

| GENERIC DRUG | DRUG CLASS | DOSE RANGE |
| --- | --- | --- |
| methohexital | barbiturate | 10–500 mg |
| pentobarbital | barbiturate | 50–200 mg |
| thiamylal | barbiturate | 10–500 mg |
| thiopental | barbiturate | 50–500 mg |
| fentanyl | opioid agonist | 0.05–5 mg |
| alfentanil | opioid agonist | 0.5–50 mg |
| sufentanil | opioid agonist | 5–500 $\mu$g |
| lofentanil | opioid agonist | 0.1–100 $\mu$g |
| carfentanil | opioid agonist | 0.2–100 $\mu$g |
| naloxone | opioid antagonist | 0.5–5 mg |
| nalbuphene | opioid antagonist | 1–50 mg |
| diazepam | benzodiazepine | 1–40 mg |
| lorazepam | benzodiazepine | 1–4 mg |
| midazolam | benzodiazepine | 0.5–25 mg |
| oxazepam | benzodiazepine | 5–40 mg |
| triazolam | benzodiazepine | 250–1000 mg |
| droperidol | buterophenone | 1–20 mg |
| haloperidol | buterophenone | 0.5–10 mg |
| propanidid | eugenol | 1–10 mg |
| etomidate | GABA stimulator | 5–60 mg |
| propofol | substituted phenol | 3–50 mg |
| ketamine | phencyclidine | 5–300 mg |
| diprivan | substituted phenol | 5–20 mg |

Drugs having effects on the cardiovascular and renal vascular systems may also be administered using a dosage-form of the present invention. A few examples of such drugs are identified in Table 2.

TABLE 2

| GENERIC DRUG | DRUG CLASS | DOSE RANGE |
| --- | --- | --- |
| Bretylium | antiarrhythmic | 50–500 mg |
| Captopril | ACE inhibitor | 25–75 mg |
| Clonidine | antihypertensive | 0.1–0.5 mg |
| Dopamine | renal vascular | 0.5–5 mg |
| Enalapril | ACE inhibitor | 5–15 mg |
| Esmolol | antihypertensive/angina | 100–250 mg |
| Furosemide | diuretic | 20.0–100 mg |
| Isosorbide | angina | 2.5–40 mg |
| Labetolol | antihypertensive | 100–400 mg |
| Lidocaine | antiarrhythmic | 50–250 mg |
| Metolazone | diuretic | 5–50 mg |
| Metoprolol | antihypertensive | 25–100 mg |
| Nadolol | antihypertensive | 40–160 mg |
| Nifedipine | antihypertensive/angina/vasodilator | 10–40 mg |
| Nitroglycerin | antihypertensive/angina | 0.4–1.0 mg |
| Nitroprusside | hypotensive | 10–50 mg |
| Propranolol | antihypertensive/angina | 0.1–50 mg |

In addition to the foregoing, there are many other drugs which can be administered using a dosage-form of the present invention. Exemplary of such drugs are those identified in Table 3.

TABLE 3

| GENERIC DRUG | DRUG CLASS | DOSE RANGE |
| --- | --- | --- |
| Benzquinamide | antiemetic | 25–100 mg |
| Meclizine | antiemetic | 25–100 mg |
| Metoclopramide | antiemetic | 5–20 mg |
| Prochlorperazine | antiemetic | 5–25 mg |
| Trimethobenzamide | antiemetic | 100–2500 mg |
| Clotrimazole | antifungal | 10–20 mg |

TABLE 3-continued

| GENERIC DRUG | DRUG CLASS | DOSE RANGE |
|---|---|---|
| Nystatin | antifungal | 100,000–500,000 units |
| Carbidopa | antiparkinson | with levodopa 10–50 mg |
| Levodopa | antiparkinson | 100–750 mg |
| Sucralfate | antisecretory | 1–2 grams |
| Albuterol | bronchodilator | 0.8–1.6 mg |
| Aminophylline | bronchodilator | 100–500 mg |
| Beclomethasone | bronchodilator | 20–50 μg |
| Dyphylline | bronchodilator | 100–400 mg |
| Epinephrine | bronchodilator | 200–500 μg |
| Flunisolide | bronchodilator | 25–50 μg |
| Isoetharine | bronchodilator | 170–680 μg |
| Isoproterenol HCl | bronchodilator | 60–260 μg |
| Metaproterenol | bronchodilator | 0.65–10 mg |
| Oxtriphylline | bronchodilator | 50–400 mg |
| Terbutaline | bronchodilator | 2.5–10 mg |
| Theophylline | bronchodilator | 50–400 mg |
| Ergotamine | antimigraine | 2–4 mg |
| Methysergide | antimigraine | 2–4 mg |
| Propranolol | antimigraine | 80–160 mg |
| Suloctidil | antimigraine | 200–300 mg |
| Ergonovine | oxytocic | 0.2–0.6 mg |
| Oxytocin | oxytocic | 5–20 units |
| Desmopressin acetate | antidiuretic | 10–50 μg |
| Lypressin | antidiuretic | 7–14 μg |
| Vasopressin | antidiuretic | 2.5–60 units |
| Insulin | antihyperglycemic | 1–100 units |

In addition to the foregoing drugs, certain macromolecular drugs (such as β-endorphin, enkephalins, bradykinin, aniotensin I, gonadotropic hormones, adrenocorticotropic hormone (ACTH), calcitonin, parathyroid hormone, and growth hormone), polysaccharides (such as heparin), antigens, antibodies, and enzymes may be adapted for transmucosal administration within the scope of the present invention.

When incorporating a drug into a nondissolvable drug containment matrix within the scope of the present invention, the amount of drug used will generally differ from the amount used in more traditional injection and oral administration techniques. Depending upon the lipophilic nature of the drug, its potency, the use of permeation enhancers, and the drug's end use, the total concentration of the drug in the typical dosage-form may contain up to 50 times more than the amount of drug which would typically be used in an injection, but it may also contain significantly less than the amount used orally, and it may also contain less than the amount used in some intramuscular injections. For purposes of example, Tables 1, 2, and 3 set forth presently contemplated ranges of the dosages of certain drugs which could be typically used.

A wide variety of drugs may be used within the scope of the present invention. The present invention allows drugs to be incorporated within the nondissolvable drug containment matrix which would otherwise be insoluble, unpleasant tasting, or have other undesirable characteristics. This capability is provided by the various formation techniques of the dosage-form. The present invention also allows lipophilic as well as nonlipophilic drugs to be utilized depending on the use of permeation enhancers.

In summary, it will be appreciated that a wide variety of drugs can be used within the scope of the present invention. At the same time, several benefits are provided. Efficient delivery of the drug is facilitated while at the same time drug degradation is avoided. The drug can also be administered in a dose-to-effect manner so that the drug effect produced is precisely controlled.

6. Summary

In summary, it can be seen that the present invention accomplishes the objects set forth above. The present invention provides compositions and methods of manufacture for administering a drug in a precise dose in order to obtain a rapid effect. In addition, the present invention provides methods for forming a drug containing nondissolvable drug containment matrix having the following attributes:

(1) drugs having relatively low melting points can be used without degrading the drug;

(2) drugs that are volatile can be incorporated into the matrix;

(3) disagreeable flavor characteristics can be masked;

(4) insoluble ingredients can be used;

(5) chemically incompatible ingredients can be used;

(6) buffer forming reagents can be added to optimize the ratio of ionized and unionized drug form;

(7) permeation enhancers can be added to increase the drug absorption;

(8) lipid soluble mixtures can be added to increase drug absorption;

(9) both lipophilic and nonlipophilic drugs can be suitably used.

The present invention, therefore, provides the ability to provide precise control over the dosage and effect of the drug. This is obtained by transmucosal administration of the drug by sucking a nondissolvable drug containment matrix or dosage-form having a handle. As a result, the precise dosage and effect can be obtained.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A drug-containing dosage-form for use in the transmucosal delivery of a drug to a patient, the dosage-form consisting essentially of:

(a) a drug containment matrix which is nondissolvable by the saliva in the mouth of the patient and which is designed to be nonfrangible in the mouth of the patient, the drug containment matrix containing a pharmacologically effective dose of a drug so that the nondissolvable drug containment matrix is capable of being sucked on or passively held within the mouth and is configured to release the drug within the mouth of the patient for adsorption through mucosal tissues of the mouth, pharynx, and esophagus, the drug containment matrix also having a holder means secured thereto, the holder means being configured to permit convenient insertion and removal of the drug containment matrix into and out of the mouth of the patient in a dose-to-effect manner; and (b) a buffer including citric acid/sodium citrate held within the drug containment matrix.

2. A drug-containing dosage-form as recited in claim 1, wherein the buffer further includes a phosphate buffer system.

3. A drug-containing dosage-form as recited in claim 1, wherein the buffer is incorporated in an amount of about 1% by weight.

4. A drug-containing dosage-form for use in the transmucosal delivery of a drug to a patient, the dosage-form consisting essentially of:

(a) a drug containment matrix which is nondissolvable by the saliva in the mouth of the patient and which is designed to be nonfrangible in the mouth of the patient, the drug containment matrix containing a pharmacologically effective dose of a drug so that the nondissolvable drug containment matrix is capable of being sucked on or passively held within the mouth and is configured to release the drug within the mouth of the patient for adsorption through mucosal tissues of the mouth, pharynx, and esophagus, the drug containment matrix also having a holder means secured thereto, the holder means being configured to permit convenient insertion and removal of the drug containment matrix into and out of the mouth of the patient in a dose-to-effect manner; and (b) a buffer including a phosphate buffer system held within the drug containment matrix.

5. A drug-containing dosage-form as recited in claim 4, wherein the buffer is incorporated in an amount of about 1% by weight.

* * * * *